United States Patent [19]

Horikawa et al.

[11] Patent Number: 5,589,592
[45] Date of Patent: Dec. 31, 1996

[54] PROCESS FOR PREPARING β-LACTAM DERIVATIVE AND SYNTHETIC INTERMEDIATE

[75] Inventors: Hiroshi Horikawa, Kawanishi; Kazuhiko Kondo, Osaka, both of Japan

[73] Assignee: Tanabe Seiyaku Co., Ltd., Osaka, Japan

[21] Appl. No.: 393,395

[22] Filed: Apr. 7, 1995

Related U.S. Application Data

[62] Division of Ser. No. 18,407, Feb. 17, 1993, Pat. No. 5,414,081.

[30] Foreign Application Priority Data

Jun. 3, 1992 [JP] Japan .................................. 4-99023

[51] Int. Cl.⁶ .................................................. C07D 503/04
[52] U.S. Cl. ............................ 540/204; 540/205; 540/214
[58] Field of Search .................................. 540/214, 204, 540/205

[56] References Cited

U.S. PATENT DOCUMENTS 4,547,371  10/1983  Doherty et al. ............................ 540/230

FOREIGN PATENT DOCUMENTS 0249358  12/1987  European Pat. Off. .

OTHER PUBLICATIONS

Gleason, J. G., et al., "Nuclear Analogs of β–Lactam Antibiotics. The Synthesis of 3–Thia–and 3–Aza–1–Dethiaceph–1–em Esters", *Tetrahedron Letters*, 21:3947–3950 (1980).

*Primary Examiner*—John M. Ford
*Assistant Examiner*—Pavanaram K. Sripada
*Attorney, Agent, or Firm*—Browdy and Neimark

[57] ABSTRACT

Disclosed is a process for preparing a β-lactam compound represented by the formula:

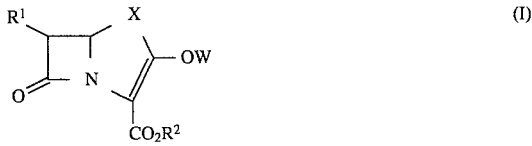

wherein $R^1$ represents a hydroxy-substituted lower alkyl group or an amino group each of which may be protected; $R^2$ represents hydrogen atom or an ester residue; X represents a methylene group which may be substituted by a lower alkyl group, sulfur atom or a group represented by the formula: $-A-CH_2-$ where A represents sulfur atom, oxygen atom or methylene group; and W represents an active ester residue of hydroxyl group, or a salt thereof, which comprises the steps of treating a 1-aza-3-thia-bicycloalkane compound represented by the formula:

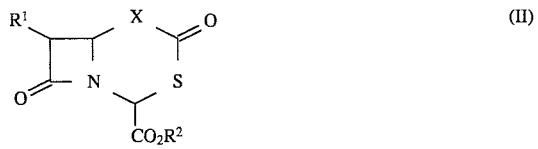

wherein $R^1$, $R^2$ and X have the same meanings as defined above, or a salt thereof with a base in the presence of a desulfurizing agent and then reacting the resulting compound with an active esterifying agent of hydroxyl group.

11 Claims, No Drawings

PROCESS FOR PREPARING β-LACTAM DERIVATIVE AND SYNTHETIC INTERMEDIATE

CROSS-REFERENCE TO RELATED APPLICATIONS

This application is a division of application Ser. No. 08/018,407, filed Feb. 17, 1993, now U.S. Pat. No. 5,414,081.

BACKGROUND OF THE INVENTION

This invention relates to a novel process for preparing a β-lactam derivative useful as a synthetic intermediate of a β-lactam type antibacterial agent having an antibacterial activity, and relates to a synthetic intermediate of said β-lactam derivative.

As a β-lactam type antibacterial agent, there have been known various compounds including a penem or carbapenem series compound such as thienamycin and imipenem, and a cephem, carbacephem or oxacephem series compound such as cephalexin.

As to processes for synthesizing these compounds, there have been known, for example, a process which proceeds through an intermediate having diphenylphosphoryloxy group at 2-position of a carbapenem skeleton described in Japanese Provisional Patent Publication No. 123182/1982 as a process for synthesizing a carbapenem (or penem) series compound, a process which proceeds through an intermediate having methanesulfonyloxy group at 3-position of a cephem skeleton described in Japanese Provisional Patent Publication No. 21685/1992 as a process for synthesizing a cephem series compound, and others. However, the conventional processes have problems to be cancelled such as many operation steps and complicated reaction operations. Thus, it has been demanded to develop a process which can prepare a desired antibacterial agent more efficiently.

SUMMARY OF THE INVENTION

An object of the present invention is to provide a novel process for preparing a β-lactam derivative useful as a synthetic intermediate of a β-lactam type antibacterial agent and a novel process for preparing a β-lactam type antibacterial agent using said derivative.

That is, the present invention relates to a novel process for preparing a β-lactam derivative represented by the following formula (I):

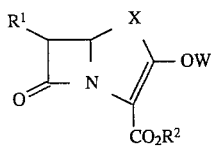
(I)

wherein $R^1$ represents a hydroxy-substituted lower alkyl group which may be protected or an amino group which may be protected; $R^2$ represents hydrogen atom or an ester residue; X represents methylene group, a methylene group substituted by a lower alkyl group, sulfur atom or a group represented by the formula: —A—CH$_2$— where A represents sulfur atom, oxygen atom or methylene group; and W represents an active ester residue of hydroxyl group,
which comprises treating a 1-aza-3-thia-bicycloalkane compound represented by the formula (II):

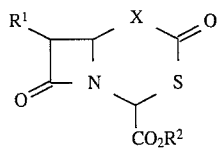
(II)

wherein the symbols have the same meanings as defined above,
or a salt thereof with a base in the presence of a desulfurizing agent and then reacting the resulting compound with an active esterifying agent of hydroxyl group.

DESCRIPTION OF THE EMBODIMENTS

In the following, the present invention is explained in detail.

In the above compound (I), as a specific example of the group $R^1$, there may be mentioned a hydroxy-substituted alkyl group having 1 to 6 carbon atoms which may be protected or an amino group which may be protected.

The group X is methylene group, a methylene group substituted by a lower alkyl group such as methyl group and ethyl group, sulfur atom or a group represented by the formula: —A—CH$_2$- where A represents sulfur atom, oxygen atom or methylene group. When the group $R^1$ is a hydroxy-substituted lower alkyl group which may be protected, X is particularly preferably a methylene group which may be substituted by a lower alkyl group or sulfur atom. When the group $R^1$ is an amino group which may be protected, the group X is particularly preferably a group represented by the formula: —S—CH$_2$—, —O—CH$_2$— or —CH$_2$CH$_2$—.

In the above compound (I), the active ester residue of hydroxyl group represented by W may include, for example, a di-lower alkylphosphoryl group or diarylphosphoryl group represented by the formula: —P(O)(OR$^0$)$_2$ (wherein R$^0$ represents a lower alkyl group or an aryl group); a substituted or unsubstituted lower alkylsulfonyl group such as methanesulfonyl group and trifluoromethanesulfonyl group; and a substituted or unsubstituted phenylsulfonyl group such as benzenesulfonyl group and p-methoxybenzenesulfonyl group.

When the group $R^1$ of the above compound (I) is a protected hydroxy-substituted lower alkyl group or a protected amino group, as a protective group for hydroxy group and amino group, there may be used any group which can be removed easily by a conventional method such as hydrolysis, acidic treatment and reduction. As such a protective group for hydroxy group, there may be mentioned, for example, a lower alkoxycarbonyl group, a halogeno lower alkoxycarbonyl group, a substituted or unsubstituted phenyl lower alkyl group (e.g. a benzyl group which may be substituted by nitro group or a lower alkoxy group), a tri-lower alkylsilyl group, and a substituted or unsubstituted phenyl lower alkoxycarbonyl group (e.g. a benzyloxycarbonyl group which may be substituted by nitro group or a lower alkoxy group).

On the other hand, as a protective group for amino group, there may be mentioned a lower alkanoyl group, a lower alkoxycarbonyl group, benzoyl group, benzenesulfonyl group, a phenyl lower alkoxycarbonyl group, a tri-lower alkylsilyl group and trityl group.

As an example of the ester residue represented by $R^2$, there may be mentioned an ester residue which is metabolized and hydrolyzed in a living body or an ester residue which can be a protective group for carboxyl group.

The ester residue metabolized and hydrolyzed in a living body may include, for example, a group represented by the formula: —Q—OCOR, —Q—OCO₂R or —Q—O—R (wherein Q represents a lower alkylene group, and R represents a lower alkyl group, a cycloalkyl group, a lower alkenoyl group, a lower alkoxy lower alkyl group or a lower alkanoyloxy lower alkyl group).

On the other hand, the ester residue which can be a protective group for carboxyl group may include, for example, a lower alkyl group, a lower alkenyl group, a halogeno lower alkyl group, a nitrobenzyl group and a lower alkoxybenzhydryl group.

In the above reaction, the compound (II) may be used in the form of a salt, and as a specific example of such a salt, there may be mentioned an alkali metal salt such as a sodium salt or a quaternary ammonium salt.

According to the present invention, the 1-aza-3-thia-bicycloalkane compound (II) can be treated with a base in the presence of a desulfurizing agent in a suitable solvent. The base may include, for example, an alkali metal alkoxide such as potassium tert-butoxide, an alkali metal amide such as lithium diisopropylamide, tri-lower alkylamine such as triethylamine, and an aromatic amine such as pyridine. As the desulfurizing agent, there may be mentioned, for example, a triarylphosphine such as triphenylphosphine, a tri-(lower alkyl)phosphite such as triethyl phosphite, a tri-lower alkylphosphine such as triethylphosphine, tris(di-lower alkylamino)phosphite and his (di-lower alkylamino-lower alkyl)phosphite. As the solvent, there may be mentioned, for example, toluene, benzene, tetrahydrofuran, diethyl ether, acetonitrile, methylene chloride, chloroform, dimethylformamide and dimethylsulfoxide. The present reaction is preferably carried under cooling to at room temperature, particularly preferably −40° C. to 0° C.

If necessary, in order to make the present reaction as mentioned above proceed more efficiently, a lithium salt such as lithium bromide and lithium perchlorate may be added to the reaction mixture.

The compound obtained by the treatment with a base in the presence of a desulfurizing agent as mentioned above is considered to have the following structure.

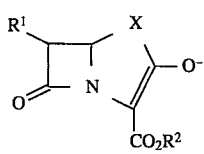

wherein the symbols have the same meanings as defined above.

The above resulting compound and an active esterifying agent of hydroxyl group may be reacted in a suitable solvent. As the active esterifying agent of hydroxyl group, there may be mentioned, for example, a reactive derivative (e.g. a corresponding acid halide and a corresponding acid anhydride) of a phosphoric acid or sulfonic acid compound including a diaryl phosphate such as diphenyl phosphate; a di-lower alkyl phosphate such as diethyl phosphate; a substituted or unsubstituted lower alkanesulfonic acid such as methanesulfonic acid and trifluoromethanesulfonic acid; and a substituted or unsubstituted benzenesulfonic acid such as benzenesulfonic acid and p-methoxybenzenesulfonic acid. As the solvent, there may be used, for example, ethyl acetate and dioxane in addition to the exemplary solvents to be used for the base treatment of the compound (II). The present reaction is preferably carried out under cooling to at room temperature, particularly preferably −40° C. to 0° C.

The β-lactam compound (I) thus obtained can be suitably converted into a desired carbapenem (or penem) type antibacterial agent or cephem type antibacterial agent.

For example, the β-lactam compound (I) can be converted into a β-lactam derivative represented by the formula (IV):

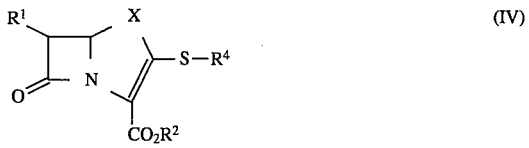

wherein R⁴ represents an organic group; and R¹, R² and X have the same meanings as defined above, by subjecting the compound (I) and a mercaptan compound represented by the formula (III):

wherein R⁴ has the same meaning as defined above, or a salt thereof to condensation reaction.

In the mercaptan compound (III) to be used in the above reaction, as an example of the organic group represented by R⁴, there may be used any group used in a conventionally known carbapenem (or penem) type antibacterial agent or cephem type antibacterial agent. As a specific example of such an organic group, there may be mentioned, for example, a lower alkyl group such as methyl and ethyl; a cycloalkyl group such as cyclohexyl group; a 6- to 8-membered aryl group such as phenyl group; a 4- to 8-membered aliphatic heterocyclic group such as pyrrolidinyl group; and a 4- to 8-membered aromatic heterocyclic group such as pyridyl group and thiazolyl group. Further, these groups may have one or more substituent(s), and as such a substituent, there may be mentioned, for example, a lower alkyl group; hydroxyl group; a lower alkoxy group; a mono- or di-lower alkylamino group; mercapto group; a lower alkylthio group; amidino group, guanidino group; carbamoyl group; thiocarbamoyl group; sulfamoyl group; cyano group; carboxyl group; a lower alkoxycarbonyl group; an aralkyloxycarbonyl group; oxo group; a halogeno group; a cycloalkyl group having 3 to 8 carbon atoms such as cyclohexyl group; a 6- to 8-membered aryl group such as phenyl group; a 4- to 8-membered aliphatic heterocyclic group such as pyrrolidinyl group; and a 4- to 8-membered aromatic heterocyclic group such as pyridyl group and thiazolyl group.

Further, as the mercaptan compound (III), there may be suitably used, in addition to the compound as described above, a compound represented by the formula (III-a) described in Japanese Provisional Patent Publication No. 279588/1992 filed by the present applicant:

wherein R⁵ represents hydrogen atom, a lower alkyl group, a lower alkoxy-lower alkyl group or a di-lower alkylamino lower alkyl group.

The above mercaptan compound (III) may be also used in the form of a salt, and as a specific example of such a salt, there may be mentioned an alkali metal salt and a tri-lower alkyl ammonium salt.

The condensation reaction of the compound (I) and the compound (III) may be carried out in a suitable solvent (e.g. toluene, benzene, acetonitrile, tetrahydrofuran, diethyl ether and ethyl acetate) in the presence or absence of a base (e.g. a tri-lower alkylamine and a 4-di-lower alkylaminopyridine).

In the compound (IV) thus obtained, when the group $R^1$ is a protected hydroxy-substituted lower alkyl group or a protected amino group, and/or when the group $R^2$ is an ester residue, the protective group and/or ester residue may be removed, if desired, to obtain a compound represented by the formula (IV-a):

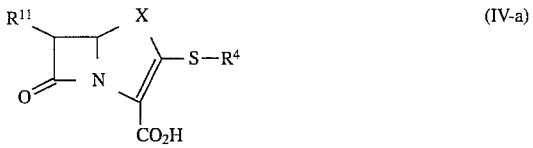

(IV-a)

wherein $R^{11}$ represents a hydroxy-substituted lower alkyl group or amino group; and other symbols have the same meanings as defined above, or a salt thereof. The protective group or ester residue may be removed according to a conventional method.

Further, the above compound (IV) in which $R^2$ is hydrogen atom or a salt thereof may be esterified by a conventional method to form a compound represented by the formula (IV-b):

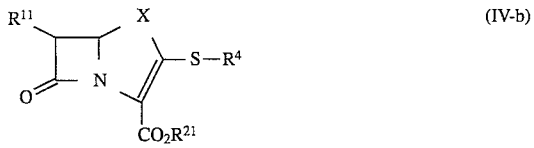

(IV-b)

wherein $R^{21}$ represents an ester residue; and other symbols have the same meanings as defined above.

Among the compounds (IV) described above, a compound in which the group $R^1$ is a hydroxy-substituted lower alkyl group which may be protected, and X is a methylene group which may be substituted by methyl group, or sulfur atom is a compound useful as a carbapenem (or penem) type antibacterial agent.

On the other hand, a compound in which the group $R^1$ is an amino group which may be protected, and X is a group represented by the formula: —A—$CH_2$— where A represents sulfur atom, oxygen atom or methylene group is a compound useful as a synthetic intermediate of a cephem, oxacephem or carbacephem type antibacterial agent, and said compound can be converted into a desired cephem type antibacterial agent according to, for example, the method described in Japanese Provisional Patent Publication No. 21685/1992.

Among the compounds (IV) described above, a 1-methylcarbapenem derivative represented by the formula (IV-c):

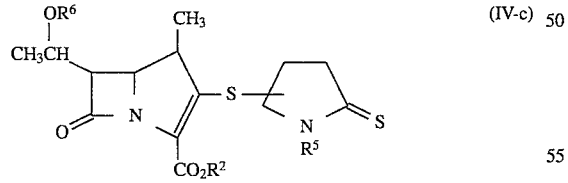

(IV-c)

wherein $R^6$ represents hydrogen atom or a protective group for hydroxyl group; and other symbols have the same meanings as defined above, which can be obtained by subjecting the compound (I) in which $R^1$ is a 1-hydroxyethyl group which may be protected and X is ethylidene group and the above mercaptan compound (III-a) to condensation reaction is a compound exhibiting various excellent characteristics such as excellent antibacterial activities to various microorganisms including gram-negative bacteria and gram-positive bacteria and high stability to dehydropeptidase I.

In the above process of the present invention, in the starting compound (II), an optical isomer based on an asymmetric carbon atom thereof may exist. And, when an optically active compound (II) is used as a starting material, a reaction can proceed while maintaining a stereo-structure to convert the compound (II) into the compound (I) and the compound (IV) without epimerization.

Further, in the reaction of converting the starting compound (II) into the compound (I) and in the subsequent reaction of converting the compound (I) into the compound (IV), the compound (I) can be isolated easily by a conventional method, but it is also possible to convert the compound (II) into the compound (IV) in the same reactor without isolation.

The starting compound (II) in the present invention is a novel compound, and said compound (II) can be prepared by, for example, (A) reacting an azetidinone compound represented by the formula (V):

(V)

wherein Z represents a protective group for thiol group; and other symbols have the same meanings as defined above, with a glyoxylate represented by the formula (VI):

$$HOCCO_2R^2 \quad (VI)$$

wherein $R^2$ has the same meaning as defined above, in a suitable solvent (e.g. benzene, chloroform and acetonitrile) under heating, or (B) reacting the compound (V) with a halogenoglyoxylate represented by the formula (VII):

$$Y^2OCCO_2R^2 \quad (VII)$$

wherein $y^2$ represents a halogen atom; and $R^2$ has the same meaning as defined above, in a suitable solvent (e.g. dichloromethane, tetrahydrofuran, acetonitrile and chloroform) in the presence of a base (e.g. 2,6-lutidine and pyridine), then reducing the resulting compound to obtain a compound represented by the formula (VIII):

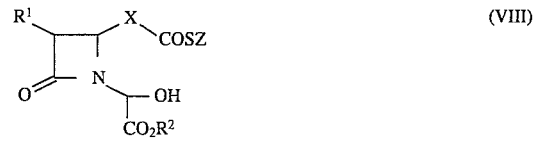

(VIII)

wherein the symbols have the same meanings as defined above, treating said compound (VIII) with a halogenating agent (e.g. thionyl chloride, thionyl bromide, phosphorus tribromide, phosphorus trichloride and methanesulfonyl chloride) in a suitable solvent (e.g. tetrahydrofuran, chloroform, benzene, acetonitrile and dichloromethane) in the presence or absence of a base (e.g. pyridine, triethylamine and dimethylaniline) to obtain a compound represented by the formula (IX):

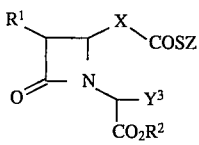

(IX)

wherein $Y^3$ represents a halogen atom; and other symbols have the same meanings as defined above, and further treating said compound (IX) with a base (e.g. a trilower alkylamine such as triethylamine, an alkali metal alkoxide such as sodium methoxide and an alkali metal amide) in a suitable solvent (e.g. dimethylformamide, dimethylsulfoxide, acetonitrile, tetrahydrofuran, ethyl ether and ethyl acetate) to effect cyclization.

The protective group (Z) for thiol group can be removed in the cyclization reaction by treating the compound (IX) with a base, and as a specific example of such a protective group Z, there may be mentioned, for example, a 2,2-bis(lower alkoxycarbonyl)ethyl group, 2,2-dicyanoethyl group, a 2-lower alkoxycarbonylethyl group and 2-cyanoethyl group.

Further, the above starting compound (V) can be prepared according to a conventional method, for example, by reacting an azetidinoncarboxylic acid compound represented by the formula (X):

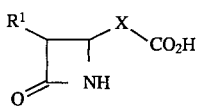

(X)

wherein the symbols have the same meanings as defined above,
with a compound represented by the formula (XI):

 (XI)

wherein Z has the same meaning as defined above, in a suitable solvent (e.g. acetonitrile) in the presence of a condensing agent (e.g. carbonyldiimidazole and dicyclohexylcarbodiimide), or reacting an acetoxyazetidine compound represented by the formula (XII):

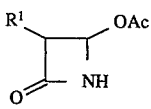

(XII)

wherein Ac represents acetyl group; and $R^1$ has the same meaning as defined above,
with a compound represented by the formula (XIII):

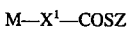 (XIII)

wherein M represents hydrogen atom, sodium atom or lithium atom; $X^1$ represents a formula: $-S-CH_2-$, $-O-CH_2-$ or $-CH_2CH_2-$; and Z has the same meaning as defined above.

In the present specification and claims, the lower alkyl group, lower alkylene group and lower alkoxy group preferably have 1 to 6 carbon atoms, the lower alkanoyl group and lower alkenyl group preferably have 2 to 8 carbon atoms, and further the lower alkenoyl group and cycloalkyl group preferably have 3 to 8 carbon atoms, respectively.

EXAMPLES

The present invention is described in detail by referring to Examples, but the scope of the invention is not limited by these Examples.

Example 1

(1) In 500 ml of acetonitrile was suspended 26.7 g of (3S,4S)-3-[(R)-1-tert-butyldimethylsilyloxyethyl]-4-[(1R)-1-carboxyethyl]-2-azetidinone, 14.6 g of carbonyldiimidazole was added thereto, and the mixture was stirred at room temperature for 30 minutes. To the reaction mixture was added 20.3 g of diethyl mercaptomethylmalonate, and the mixture was stirred at room temperature for 20 minutes. The solvent was removed from the reaction mixture under reduced pressure. After 500 ml of diethyl ether was added to the residue and the mixture was washed and dried, the solvent was removed under reduced pressure. The residue was purified by silica gel column chromatography (solvent; ethyl acetate:n-hexane=1:3) to obtain 33 g of (3S,4S)-3-[(R)-1-tert-butyldimethylsilyloxyethyl]-4-[(1R) -1-{2,2-bis)ethoxycarbonyl)ethylthiocarbonyl}ethyl]-2-azetidinone.

IR (KBr) $cm^{-1}$: 3080, 1765, 1735, 1690.

Mass (m/z): 432 ($M^+$-57).

NMR ($CDCl_3$) δ: 0.07 (s, 6H), 1.15 (d, 3H, J=6.2 Hz), 1.24 (d, 3H, J=6.8 Hz), 1.28 (t, 3H, J=7.0 Hz), 2.8 to 3.0 (m, 1H), 3.34 (d, 1H, J=2.4 Hz), 3.38 (d, 1H, J=2.4 Hz), 3.8 to 3.9 (m, 1H), 4.2 to 4.3 (m, 5H), 5.62 (br s, 1H).

(2) In 10 ml of benzene were dissolved 1 g of the product obtained above and 0.76 g of ethyl glyoxylate, and the mixture was refluxed by heating for 2 hours in a reactor equipped with a cooling tube charged with 10 g of Molecular Sieve 4A (trade name, produced by Nacalai tesque INC.). After the reaction mixture was diluted with ethyl acetate, washed and dried, the solvent was removed. The residue was purified by silica gel column chromatography (solvent; ethyl acetate:n-hexane=1:3) to obtain 1.0 g of (3S,4S)-3-[(R)-1-tert-butyldimethylsilyloxyethyl]-4 -[(1R) -1-{2,2-bis(ethoxycarbonyl)ethylthiocarbonyl)}ethyl]-1-(1-hydroxy-1-ethoxycarbonylmethyl)-2-azetidinone.

IR (film) $cm^{-1}$: 3450, 1770, 1748, 1690.

Mass (m/z): 534 ($M^+$-57).

NMR ($CDCl_3$) δ: 0.60+0.08 (s+s, 6H), 0.87+0.88 (s+s, 9H), 1.2 to 1.4 (m, 15H), 2.9 to 3.1 (m, 2H), 3.3 to 3.4 (m, 2H), 3.62 (t, 1H, J=7.8 Hz), 4.0 to 4.4 (m, 9H), 5.30+5.46 (d+d, 1H, J=8.4 Hz).

(3) To 10 ml of tetrahydrofuran solution containing 0.78 g of the product obtained above were added dropwise 0.21 ml of pyridine and 0.17 ml of thionyl chloride at −50° C., and the mixture was stirred at −50° to −40° C. for 30 minutes. After the reaction mixture was diluted with ethyl acetate and washed, an organic layer was collected by separation. The organic layer was dried, and then the solvent was removed. The residue [(3S,4S)-3-[(R)-1-tert-butyldimethylsilyloxyethyl]-4-[(1R)-1-{2,2-bis(ethoxycarbonyl)ethylthiocarbonyl}ethyl]-1-(1-chloro-1 -ethoxycarbonylmethyl)-2-azetidinone] (0.8 g) was dissolved in dimethylformamide. To the solution was added 0.21 ml of triethylamine at −20° C., and the mixture was stirred at −20° to 0° C. for 1 hour. After 10 ml of ethyl acetate was added to the reaction mixture, the mixture was washed and an organic layer was collected by separation. After the organic layer was dried, the solvent was removed. The residue was purified by silica gel column chromatography (solvent; ethyl acet-ate:n-hexane=1:5) to obtain 0.20 g of ethyl (5R,6S,7S)-7-[(R)-1-tert-butyldimethylsilyloxyethyl]-5-methyl-4,8-dioxo-1-aza-3-thia-bicyclo[4.2.0]octan-2-carboxylate.

IR (film) $cm^{-1}$: 1779, 1745, 1690.

Mass (m/z): 486 ($M^+$-15), 344 ($M^+$-57).

NMR ($CDCl_3$) δ: 0.08 (s, 3H), 0.10 (s, 3H), 0.87 (s, 9H), 1.20 (d, 3H, J=6.4 Hz), 1.23 (d, 3H, J=6.8 Hz), 2.92 (dd, 1H,

J=4.6 Hz, 3.0 Hz), 3.56 (quintet, 1H, J=6.8 Hz), 4.1 to 4.3 (m, 1H), 4.29 (q, 2H, J=7.2 Hz), 4.54 (dd, 1H, J=3.0 Hz), 5.79 (s, 1H).

(4) In 1 ml of toluene were dissolved 20 mg of the product obtained above and 16 mg of triphenylphosphine, to the solution was added 7 mg of potassium tert-butoxide at −40° C., and the mixture was stirred at −40° to −20° C. for 30 minutes. To the reaction mixture was added a solution of 15 mg of diphenyl chlorophosphate dissolved in 0.5 ml of acetonitrile at the same temperature, and a temperature of the mixture was elevated gradually up to 0° C. The reaction mixture was condensed, and the residue was purified by thin layer chromatography (solvent; ethyl acetate:n-hexane =1:4) to obtain 20 mg of ethyl (1R,5S,6S)-6-[(R)-1-tert-butyldimethylsilyloxyethyl]-2-diphenylphosphoryloxy-1-methylcarbapen-2-em-3-carboxylate (an oily product).

Mass (m/z): 601 (M$^+$), 544 (M$^+$-57).

NMR(CDCl$_3$) δ: 0.06 (s, 6H), 0.87 (s, 9H), 1.1 to 1.3 (m, 9H), 3.23 (dd, 1H, J=6.2 Hz, 3.0 Hz), 3.3 to 3.5 (m, 1H), 4.0 to 4.4 (m, 1H), 7.1 to 7.4 (m, 10H).

Example 2

(1) The corresponding compound was treated in the same manner as in Example 1 (2) to obtain (3S,4S)-3-[(R)-1-tert-butyldimethylsilyloxyethyl]-4-[(1R)-1-{2,2-bis(ethoxycarbonyl)ethylthiocarbonyl}ethyl]-1-(1-hydroxy-1-p-nitrobenzyloxycarbonylmethyl)-2-azetidinone.

NMR(CDCl$_3$) δ: 0.0 to 0.10 (m, 6H), 0.86 (s, 9H), 1.1 to 1.3 (m, 12H), 2.9 to 3.1 (m, 2H), 3.3 to 3.5 (m, 2H), 3.5 to 3.7 (m, 1H), 4.0 to 4.5 (m, 7H), 5.3 to 5.6 (m, 3H), 7.5 to 7.6 (m, 2H), 8.2 to 8.3 (m, 2H).

(2) The product obtained above was treated in the same manner as in Example 1 (3) to obtain p-nitrobenzyl (5R,6S,7S)-7-[(R)-1-tert-butyldimethylsilyloxyethyl]-5-methyl-4,8-dioxo-1-aza-3-thia-bicyclo[4.2.0]octan-2-carboxylate.

IR (film) cm$^{-1}$: 1786, 1742, 1682.

Mass (m/z): 451 (M$^+$-57).

NMR(CDCl$_3$) δ: 0.05 (s, 3H), 0.07 (s, 3H), 0.86 (s, 9H), 1.20 (d, 3H, J=6.2 Hz), 1.22 (d, 3H, J=6.7 Hz), 2.95 (dd, 1H, J=4.6 Hz, 3.0 Hz), 3.49 (quintet, 3H, J=6.7 Hz), 4.0 to 4.3 (m, 2H), 4.55 (dd, 1H, J=7.1 Hz, 3.0 Hz), 5.31 and 5.37 (ABq, 2H, J=13.1 Hz), 5.90 (s, 1H), 7.53 (d, 2H, J=8.8 Hz), 8.26 (d, 2H, J=8.8 Hz).

(3) The product obtained above was treated in the same manner as in Example 1 (4) to obtain p-nitrobenzyl (1R,5S,6S)-6-[(R)-1-tert-butyldimethylsilyloxyethyl]-2-diphenylphosphoryloxy-1-methylcarbapen-2-em-3-carboxylate.

NMR(CDCl$_3$) δ: 0.06 to 0.07 (m, 6H), 0.87 (s, 9H), 1.2 to 1.3 (m, 6H), 3.27 (dd, 1H, J=5.6 Hz, 3.0 Hz), 3.3 to 3.6 (m, 1H), 4.1 to 4.3 (m, 2H), 5.23 and 5.34 (ABq, 2H, J=13.8 Hz), 7.0 to 7.6 (m, 10H), 7.55 (d, 2H, J=8.8 Hz), 8.13 (d, 2H, J=8.8 Hz).

Example 3

(1) In dichloromethane were dissolved 1.4 g of (3S,4S)-3-[(R)-1-tert-butyldimethylsilyloxyethyl]-4-[(1R)-1-{2,2-bis(ethoxycarbonyl)ethylthiocarbonyl}ethyl]-2-azetidinone and 0.64 g of pivaloyloxymethyloxalyl chloride, to the solution were added 0.34 ml of 2,6-lutidine and 10 mg of N,N-dimethylaminopyridine under ice cooling, and the mixture was stirred at the same temperature for 30 minutes. To the reaction mixture were further added 0.64 g of (3S,4S)-3-[(R)-1-tert-butyldimethylsilyloxyethyl]-4-[(1R)-1-{2,2-bis(ethoxycarbonyl)ethylthiocarbonyl}ethyl]-2-azetidinone and 0.34 ml of 2,6-lutidine, and the mixture was stirred for 30 minutes. The reaction mixture was poured into 100 ml of a 0.1M phosphate buffer (pH 7) and extracted with dichloromethane. After the extract was washed and dried, the solvent was removed under reduced pressure. The residue was purified by silica gel column chromatography (solvent; ethyl acetate:n-hexane=1:4) to obtain 1.72 g of (3S,4S)-3-[(R)-1-tert-butyldimethylsilyloxyethyl]-4-[(1R)-1-{2,2-bis(ethoxycarbonyl)ethylthiocarbonyl}ethyl]-1-pivaloyloxymethyloxyoxalyl-2-azetidinone.

IR (KBr) cm$^{-1}$: 1809, 1752, 1732, 1701.

Mass (m/z): 618 (M$^+$-57).

NMR(CDCl$_3$) δ: 0.00 (s, 3H), 0.06 (s, 3H), 0.83 (S, 9H), 1.17 (d, 3H, J=6.4 Hz), 1.23 (s, 9H), 1.28 (t, 6H, J=7.0 Hz), 1.29 (d, 3H, J=7.0 Hz), 3.2 to 3.6 (m, 5H), 4.2 to 4.4 (m, 1H), 4.25 (q, 4H, J=7.0 Hz), 4.4 to 4.5 (m 1H), 5.90 (s, 2H).

(2) In a mixed solution of 10 ml of acetic acid and 10 ml of dichloromethane was dissolved 1.7 g of the product obtained above, to the solution was added 5 g of zinc under ice cooling, and the mixture was stirred for 30 minutes. Insolubles were removed by filtration using celite, and the filtrate was removed under reduced pressure. The residue was extracted with dichloromethane. After the extract was washed and dried, the solvent was removed under reduced pressure. The residue was purified by silica gel column chromatography (solvent; ethyl acetate:n-hexane=1:3) to obtain 1.52 g of (3S,4S)-3-[(R)-1-tert-butyldimethylsilyloxyethyl]-4-[(1R)-1-{2,2-bis(ethoxycarbonyl)ethylthiocarbonyl}ethyl]-1-[1-hydroxy-1-(pivaloyloxymethyloxycarbonyl)methyl]-2-azetidinone.

IR (KBr) cm$^{-1}$: 3460, 1754, 1692.

Mass (m/z): 620 (M$^+$-57).

NMR (CDCl$_3$) δ: 0.08 (s, 6H), 0.88 (s, 9H), 1.22 (s, 9H), 1.1 to 1.4 (m, 18H), 2.9 to 3.1 (m, 2H), 3.38 (dd, 1H, J=2.4 Hz, 7.4 Hz), 3.61 (t, 1H, J=7.1 Hz), 4.0 to 4.3 (m, 7H), 4.43 (d, 1H, J=8.8 Hz), 5.30+5.52 (d+d, 1H, J=8.8 Hz), 5.7 to 5.9 (m, 2H).

(3) The product obtained above was treated in the same manner as in Example 1 (3) to obtain pivaloyloxymethyl (5R,6S,7R)-[(R)-1-tert-butyldimethylsilyloxyethyl]-5-methyl-4,8-dioxo-1-aza-3-thia-bicyclo[4.2.0]octan-2-carboxylate.

IR (KBr) cm$^{-1}$: 1765, 1691.

Mass (m/z): 472 (M$^+$-15), 430 (M$^+$-57).

NMR (CDCl$_3$) δ: 0.06 (s, 3H), 0.88 (s, 3H), 0.87 (s, 9H), 1.21 (s, 9H), 1.1 to 1.3 (m, 6H), 2.9 to 3.0 (m, 1H), 3.4 to 3.6 (m, 1H), 4.1 to 4.3 (m, 1H), 4.5 to 4.6 (m, 1H), 5.81 (d, 1H, J=5.2 Hz), 5.83 (s, 1H), 5.91 (d, 1H, J=5.2 Hz).

(4) The product obtained above was treated in the same manner as in Example 1 (4) to obtain pivaloyloxymethyl (1R,5S,6S)-6-[(R)-1-tert-butyldimethylsilyloxyethyl]-2-diphenylphosphoryloxy-1-methylcarbapen-2-em-3-carboxylate.

Mass (m/z): 687 (M$^+$), 630 (M$^+$-57).

NMR (CDCl$_3$) δ: 0.06 (s, 6H), 0.86 (s, 9H), 1.1 to 1.3 (m, 15H), 3.2 to 3.3 (m, 1H), 3.3 to 3.6 (m, 1H), 4.1 to 4.3 (m, 2H), 5.79 (d, 2H, J=1.4 Hz), 7.2 to 7.4 (m, 10H).

Example 4

(1) The corresponding compound was treated in the same manner as in Example 3 (1) to obtain (3S,4S)-3-[(R)-1-tert-butyldimethylsilyloxyethyl]-4-[(1R)-1-{2,2- bis(ethoxycarbonyl)ethylthiocarbonyl}ethyl]-1-isobutyryloxymethyloxyoxalyl-2-azetidinone.

IR (film) cm$^{-1}$: 1810, 1753, 1737, 1705.

Mass (m/z): 604 (M$^+$-57).

NMR (CDCl$_3$) δ: 0.07 (s, 3H), 0.58 (s, 3H), 0.83 (s, 9H), 1.1 to 1.4 (m, 18H), 2.5 to 2.8 (m, 1H), 3.2 to 3.7 (m, 5H), 4.1 to 4.5 (m, 6H), 5.90 (s, 2).

(2) The product obtained above was treated in the same manner as in Example 3 (2) to obtain (3S,4S)-3-[(R)-1-tert-butyldimethylsilyloxyethyl]-4-[(1R)-1-{2,2-bis(ethoxycarbonyl)ethylthiocarbonyl}ethyl]-1-[1-hydroxy-1-(isobutyryloxymethyloxycarbonyl)methyl]-2-azetidinone.

IR (KBr) cm$^{-1}$: 3437, 1754, 1685.

Mass (m/z): 606 (M$^+$-57).

NMR (CDCl$_3$) δ: 0.08 (s, 6H), 0.88 (s, 9H), 1.1 to 1.4 (m, 18H), 2.5 to 2.7 (m, 1H), 2.9 to 3.2 (m, 2H), 3.3 to 3.5 (m, 2H), 3.5 to 3.7 (m, 1H), 4.0 to 4.5 (m, 7H), 5.3 to 5.6 (m, 1H), 5.7 to 6.0 (m, 2H).

(3) The product obtained above was treated in the same manner as in Example 1 (3) to obtain isobutyryloxymethyl (5R,6S,7S)-7-[(R)-1-tert-butyldimethylsilyloxyethyl]-5-methyl-4,8-dioxo-1-aza-3-thia-bicyclo[4.2.0]octan-2-carboxylate.

IR (KBr) cm$^{-1}$: 1766, 1691, 1471.

Mass (m/z): 416 (M$^+$-57).

NMR (CDCl$_3$) δ: 0.06 (s, 3H), 0.08 (s, 3H), 0.87 (s, 9H), 1.1 to 1.3 (m, 12H), 2.61 (m, 1H), 2.93 (dd, 1H, J=3.0 Hz, 4.8 Hz), 4.23 (m, 1H), 4.55 (dd, 1H, J=2.9 Hz, 7.2 Hz), 5.82 (d, 1H, J=5.5 Hz), 5.83 (s, 1H), 5.90 (d, 1H, J=5.5 Hz).

(4) The product obtained above was treated in the same manner as in Example 1 (4) to obtain isobutyryloxymethyl (1R,5S,6S)-6-[(R)-1-tert-butyldimethylsilyloxyethyl]-2-diphenylphosphoryloxy-1-methylcarbapen-2-em-3-carboxylate.

IR (film) cm$^{-1}$: 1780, 1762, 1490.

Mass (m/z): 658 (M$^+$-15), 616 (M$^+$-57).

NMR (CDCl$_3$) δ: 0.06 (s, 6H), 0.87 (s, 9H), 1.1 to 1.3 (m, 12H), 2.55 (m, 1H), 3.23 (dd, 1H, J=2.9 Hz, 6.2 Hz), 3.44 (m, 1H), 4.0 to 4.6 (m, 1H), 7.2 to 7.5 (m, 10H).

Example 5

(1) The corresponding compound was treated in the same manner as in Example 1 (2) to obtain (3S,4S)-3-[(R)-1-tert-butyldimethylsilyloxyethyl]-4-[(1R)-2-{2,2-bis(ethoxycarbonyl)ethylthiocarbonyl}ethyl]-1-(1-hydroxy-1-allyloxycarbonylmethyl)-2-azetidinone.

NMR (CDCl$_3$) δ: 0.0 to 0.10 (m, 6H), 0.86 (s, 9H), 1.1 to 1.3 (m, 12H), 2.9 to 3.1 (m, 2H), 3.3 to 3.4 (m, 2H), 3.5 to 3.7 (m, 1H), 4.0 to 4.5 (m, 7H), 4.6 to 4.8 (m, 2H), 5.2 to 5.6 (m, 3H), 5.9 to 6.1 (m, 1H).

(2) The product obtained above was treated in the same manner as in Example 1 (3) to obtain allyl (5R,6S,7S)-7-[(R)-1-tert-butyldimethylsilyloxyethyl]-5-methyl-4,8-dioxo-1-aza-3-thia-bicyclo[4.2.0]octan-2-carboxylate.

IR (film) cm$^{-1}$: 1779, 1745, 1690.

Mass (m/z): 356 (M$^+$-57).

NMR (CDCl$_3$) δ: 0.63 (s, 3H), 0.78 (s, 3H), 0.87 (s, 9H), 1.21 (d, 3H, J=6.2 Hz), 1.23 (d, 3H, J=6.7 Hz), 2.93 (dd, 1H, J=4.7, 2.9 Hz), 3.55 (quintet, 1H, J=6.7 Hz), 4.1 to 4.3 (m, 1H), 4.55 (dd, 1H, J=7.2, 2.9 Hz), 4.6 to 4.8 (m, 2H), 5.3 to 5.5 (m, 2H), 5.84 (s, 1H), 5.8 to 6.0 (m, 1H).

Example 6

(1) In 300 ml of tetrahydrofuran was suspended 4.5 g of (4R)-4-hydroxy-2-pyrrolidone, 23.4 g of triphenylphosphine was added thereto, and the mixture was stirred for 10 minutes. Subsequently, 14 ml of diethyl azodicarboxylate was added dropwise to the reaction mixture at −10° C., and the mixture was stirred at the same temperature for 10 minutes. After 6.3 ml of thioacetic acid was added dropwise to the reaction mixture at −10° C. or lower, the mixture was stirred at the same temperature for 2 hours and the solvent was removed. The residue was crystallized from diisopropyl ether. After the crystals were removed by filtration, the filtrate was condensed under reduced pressure. The residue was purified by silica gel column chromatography (solvent; chloroform:ethanol=98:2) to obtain 3.8 g of (4S)-4-acetylthio-2-pyrrolidone as an oily product.

NMR (CDCl$_3$) δ: 2.29 (dd, 1H), 2.35 (s, 3H), 2.81 (dd, 1H), 3.31 (dd, 1H), 3.88 (dd, 1H), 4.10 to 4.23 (m, 1H), 7.02 to 7.17 (b, 1H).

(2) After a mixture of 4.8 g of the product obtained above, 100 ml of toluene and 6.1 g of Lawesson's reagent (i.e. 2,4-bis(4-methoxyphenyl)-1,3-dithia-2,4-diphosphetan-2,4-disulfide) was refluxed under heating for 15 minutes, the solvent was removed. The residue was purified by silica gel column chromatography (solvent; chloroform:ethyl acetate=5:5) to obtain 3.6 g of (4S)-acetylthiopyrrolidin-2-thione as colorless needle crystal.

m.p.: 91° to 92° C.

[α]$_D^{20}$ −57.5° (c=1, methanol).

(3) A mixture of 3.6 g of the product obtained above and 36 ml of a 16% ammonia-methanol solution was stirred under ice cooling for 30 minutes. After the solvent was removed from the reaction mixture, 36 ml of toluene was added to the residue and the mixture was condensed to obtain 2.7 g of (4S)-4-mercaptopyrrolidin-2-thione as a crude product. This product was used without purification in the next step.

(4) In 1 ml of acetonitrile was dissolved 20 mg of pivaloyloxymethyl (1R,5S,6S)-6-[(R)-1-tert-butyldimethylsilyloxyethyl]-2-diphenylphosphoryloxy-1-methylcarbapen-2-em-3-carboxylate, 4.3 mg of (4S)-4-mercaptopyrrolidin-2-thione obtained in the above (3) and 4.1 mg of N,N-diisopropylethylamine were added thereto under nitrogen gas at −20° C., and the mixture was stirred for 2 hours while gradually elevating a temperature thereof to 0° C. The reaction mixture was poured into a 0.1M phosphate buffer (pH 7) and extracted with ethyl acetate. After the extract was washed and dried, the solvent was removed under reduced pressure. The residue was purified by thin layer chromatography (solvent; ethyl acetate:n-hexane=5:5) to obtain 7 mg of pivaloyloxymethyl (1R, 5S, 6S)-6-[(R)-1-tert-butyldimethylsilyloxyethyl]-2-[(4R)-pyrrolidin-2-thion-4-ylthio]-1-methylcarbapen-2-em-3-carboxylate as colorless crystal.

m.p.: 143° C.

Mass (m/z): 536 (M$^+$-34).

Example 7

(1) In 10 ml of toluene were dissolved 500 mg of isobutyryloxymethyl (5R,6S,7S)-7-[(R)-1-tert-butyldimethylsilyloxymethyl]-5-methyl-4,8-diozo-1-aza-3-thia-bicyclo-[4.2.0]octan-2-carboxylate and 277 mg of triphenylphosphine, 130 mg of potassium tert-butoxide was added thereto under nitrogen gas at −40° C. while stirring, and the mixture was stirred at the same temperature for 50 minutes. To the reaction mixture was added dropwise 10 ml of acetonitrile solution containing 312 mg of diphenyl chlorophosphate at −40° C., and the mixture was stirred for 40 minutes. To the reaction mixture were added 155 mg of (4S)-4-mercapto-pyrrolidin-2-thione and 148 mg of diisopropylethylamine, and the mixture was stirred at −20° C. for 80 minutes, and then at −5° C. for 1.5 hours. The reaction mixture was poured into a 0.1M phosphate buffer (pH 7.0) and extracted with ethyl acetate. After the extract was washed and dried, the solvent was removed under reduced pressure. The residue was purified by silica gel column chromatography (solvent; n-hexane:ethyl acetate:chloroform =5:5:1) to obtain 248 mg of isobutyryloxymethyl (1R,5S, 6S)-6-[(R)-1-tert-butyldimethylsilyloxyethyl]-2-[(4R)-pyrrolidin-2-thion-4-ylthio]-1-methylcarbapen-2-em-3-carboxylate.

m.p.: 142° C. (decomposed).

IR (KBr) cm$^{-1}$: 3347, 1771, 1590, 1537.

(2) In 0.2 ml of tetrahydrofuran was dissolved 10 mg of the product obtained above, 0.006 ml of acetic acid and 0.072 ml of tetrahydrofuran solution containing 1M of tetrabutylammonium fluoride were added thereto, and the mixture was stirred at room temperature for 3 days. After the reaction mixture was diluted with ethyl acetate and then washed, an organic layer was collected by separation. After the organic layer was dried, the solvent was condensed under reduced pressure. The residue was purified by silica gel column chromatography (solvent; ethyl acetate) to obtain 5 mg of isobutyryloxymethyl (1R,5S,6S)-2-[(4R)-pyrrolidine-2-thion-4-ylthio]-6-[(1R)-1-hydroxyethyl]-1-methylcarbapen-2-em-3-carboxylate as colorless needle crystal.

m.p.: 158° to 159° C.

Reference example 1

(1) A mixture of 80 g of diethyl malonate, 30 g of paraformaldehyde, 5 g of potassium acetate, 5 g of copper (II) acetate monohydrate and 200 ml of acetic acid was heated at 90° to 100° C. for 2 hours. Acetic acid was removed from the reaction mixture under reduced pressure, and the residue was evaporated under reduced pressure to obtain 44 g of bis(ethoxycarbonyl)ethylene.

b.p.: 90° to 93° C. (1.3 mmHg).

(2) The product obtained above was added dropwise to 500 ml of tetrahydrofuran solution containing 22 g of thioacetic acid and 500 mg of potassium thioacetate under ice cooling and stirring. The solvent was removed from the reaction mixture. After diethyl ether was added to the residue, the mixture was washed and dried and the solvent was removed. To the residue was added 2N hydrochloric acid-ethanol, and the mixture was stirred at room temperature for 14 hours. The solvent was removed from the reaction mixture, and the residue was evaporated under reduced pressure to obtain 18.3 g of diethyl mercaptomethylmalonate.

b.p.: 78° to 82° C. (1 mmHg).

$^1$H-NMR (CDCl$_3$) δ1.29 (t, 6H, J=7.1 Hz), 1.73 (t, 1H, J=8.9 Hz), 3.00 (dd, 2H, J=8.9 Hz, 7.3 Hz), 3.57 (t, 1H, J=7.3 Hz), 4.23 (q, 4H, J=7.1 Hz).

Reference example 2

(1) To 425 g of isobutyryl chloride were added 850 mg of zinc chloride and 119 g of paraformaldehyde, and the mixture was heated at 90° to 100° C. for 8 hours. The reaction mixture was evaporated (three times), and the fractions having a boiling point of 120° to 130° C. were collected to obtain 311 g of chloromethyl isobutyrate.

(2) In 4 l of acetone were dissolved 3.53 kg of monobenzyl oxalate.tetra n-butyl ammonium salt and 1.13 kg of chloromethyl isobutyrate prepared in the above (1), and the solution was stirred overnight. Acetone was removed from the reaction mixture under reduced pressure, and the residue was dissolved in ethyl acetate. After the solution was washed and dried, the solvent was removed to obtain 2.22 kg of benzylisobutyloxymethyl oxalate (a pale yellowish oily product).

IR (film) cm$^{-1}$: 1754.

Mass (m/z): 290 (M$^+$).

(3) In 200 ml of ethyl acetate was dissolved 28 g of the product obtained above, 5 g of 10% palladium-carbon was added thereto, and the mixture was subjected to catalytic reduction under pressure for 8 hours. The catalyst was removed by filtration from the reaction mixture, and the filtrate was condensed to obtain 18 g of monoisobutyryloxymethyl oxalate (a colorless oily product).

IR (film) cm$^{-1}$: 1756.

Mass (m/z): 190 (M$^+$).

(4) In 200 ml of methylene chloride was dissolved 26 g of the product obtained above, to the solution was added 17 g of oxalyl chloride, and the mixture was stirred at room temperature for 3 hours. The reaction mixture was condensed, and 50 ml of benzene was added to the residue and removed under reduced pressure (three times). Then, the residue was evaporated to obtain 15 g of oxalic acid chloride isobutyryloxymethyl ester (a colorless oily product).

b.p.: 78° to 80° C. (1 mmHg).

IR (film) cm$^{-1}$: 1768.

Mass (m/z): 208 (M$^+$).

According to the process of the present invention, by using the novel compound 1-aza-3-thia-bicycloalkane compound (II) as a starting compound, the β-lactam derivative (I) useful as a synthetic intermediate of carbapenem (or penem) type and cephem type antibacterial agents and the compound (IV) useful as an antibacterial agent can be prepared by simple and easy operations with good efficiency.

For example, the process of the present invention has a characteristic that base treatment in the presence of the above desulfurizing agent and active esterification of the compound (II), and subsequent condensation reaction with the mercaptan compound (III) can be carried out in the same reactor.

In a conventional process described in Japanese Provisional Patent Publication No. 123182/1982, when the compound (IV) in which the group represented by R$^2$ is an easily eliminatable ester residue such as isobutyryloxymethyl group is prepared, if a corresponding starting compound in which R$^2$ is such an ester residue is used, there is a problem that said ester residue is eliminated during reaction operation. However, in the process of the present invention, the ester residue is not eliminated during reaction operation, so that the desired compound (IV) can be obtained with good efficiency.

Further, the process of the present invention also has a characteristic that the process proceeds not through a diazo compound type intermediate used in the process described in Japanese Provisional Patent Publication No. 123182/1982, so that the process can be carried out without using an azide compound such as sulfonylazide which should be handled carefully.

Furthermore, the carbapenem compound (IV-c) derived from the β-lactam derivative (I) of the present invention or a pharmacologically or pharmaceutically acceptable salt thereof is a novel compound having various extremely excellent characteristics as an antibacterial agent.

For example, the compound (IV-c) or a pharmacologically acceptable salt thereof has an excellent antibacterial activity to various microorganisms including gram-positive bacteria and gram-negative bacteria such as Escherichia, Staphylococcus and Pseudomonas, and also has a high antibacterial activity to pathogenic clinically separated strains. Thus, the compound (IV-c) or a pharmacologically acceptable salt thereof exhibits an excellent therapeutic effect on infectious diseases.

The compound (IV-c) has stronger antibacterial activities to *Staphylococcus aureus, Staphylococcus epidermidis, Escherichia coli, Proteus vulgaris* and *Pseudomonas aeruginosa*, 2-fold to 4-fold or more than those of the compound in which a substituent at 2-position is 2-oxypyrrolidin-4-ylthio group described in Japanese Provisional Patent Publication No. 49783/1990.

Further, the compound (IV-c) or a pharmacologically acceptable salt thereof has an excellent characteristic of exhibiting higher stability to dehydropeptidase I by using 2-thioxopyrrolidin-4-ylthio group at 2-position of a 1-methylcarbapenem skeleton.

For example, the compound (IV-c) exhibits more excellent stability to dehydropeptidase I, by 2-fold or more as compared with the compound described in the above Japanese Provisional Patent Publication No. 49783/1990.

Also, the compound (IV-c) or a pharmaceutically acceptable salt thereof has characteristics of having high oral absorption property and exhibiting a high therapeutic effect.

For example, when the compound (IV-c) is orally administered to a mouse infected with *Staphylococcus aureus*, a higher therapeutic effect by 2-fold to 8-fold is exhibited as compared with the case when the compound described in the above Japanese Provisional Patent Publication No. 49783/1990 is orally administered.

Further, the compound (IV-c) or a pharmacologically acceptable salt thereof has high transition property to bile, and therefore is particularly available for biliary infections.

Also, the compound (IV-c) or a pharmacologically acceptable salt thereof has low toxicity and has high safety as a medicine.

We claim:

1. A 1-aza-3-thia-bicycloalkane compound represented by the formula:

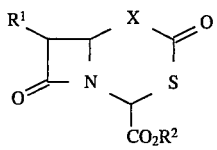

(II)

wherein $R^1$ represents a hydroxy-substituted lower alkyl group which may be protected or an amino group which may be protected; $R^2$ represents hydrogen atom or an ester residue; X represents a methylene, a methylene group substituted by a lower alkyl group, sulfur atom or a group represented by the formula: —A—CH$_2$— where A represents sulfur atom, oxygen atom or methylene group; or a salt thereof.

2. The compound according to claim 1, wherein $R^1$ is a 1-hydroxyethyl group which may be protected, and X is ethylidene group.

3. The compound according to claim 1, wherein $R^1$ is an amino group which may be protected, and X is a group represented by the formula: —S—CH$_2$—, —O—CH$_2$— or —CH$_2$CH$_2$—.

4. A 1-aza-3-thia-bicycloalkane compound represented by the formula:

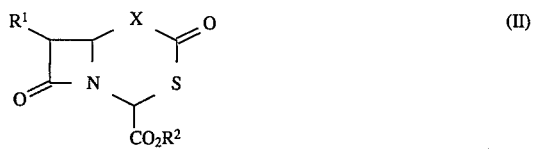

(II)

wherein:
$R^1$ represents
a hydroxy-substituted lower alkyl group which may be protected by a group selected from group consisting of a lower alkoxycarbonyl group, a halogeno lower alkoxycarbonyl group, a phenyl lower alkyl group which may be substituted by a nitro group or a lower alkoxy group, a tri-lower alkylsilyl group, and a phenyl lower alkoxycarbonyl group which may be substituted by a nitro group or a lower alkoxy group, or
an amino group which may be protected by a group selected from the group consisting of a lower alkanoyl group, a lower alkoxycarbonyl group, a benzoyl group, a benzenesulfonyl group, a phenyl lower alkoxycarbonyl group, a tri-lower alkylsilyl group and a trityl group:

$R^2$ represents a hydrogen atom, a group of the formula

—O—OCOR, —O—OCO$_2$R or —O—O—R wherein O represents a lower alkylene group, and R represents a lower alkyl group, a cycloalkyl group of 3 to 8 carbon atoms, a lower alkenoyl group, a lower alkoxy lower alkyl group, or a lower alkanoyloxy lower alkyl group,
a lower alkyl group, a lower alkenyl group, a halogeno lower alkyl group, a nitrobenzyl group or a lower alkoxybenzhydryl group; and X represents a methylene group substituted by a lower alkyl group;

or an alkali metal salt thereof.

5. The compound according to claim 4, wherein $R^1$ is a 1-hydroxyethyl group which may be protected by a group selected from group consisting of a lower alkoxycarbonyl group, a halogeno lower alkoxycarbonyl group, a phenyl lower alkyl group which may be substituted by a nitro group or a lower alkoxy group, a tri-lower alkylsilyl group, and a phenyl lower alkoxycarbonyl group which may be substituted by a nitro group or a lower alkoxy group and X is ethylidene group.

6. The compound according to claim 4, wherein $R^1$ is an amino group which may be protected by a group selected from the group consisting of a lower alkanoyl group, a lower alkoxycarbonyl group, a benzoyl group, a benezenesulfonyl group, a phenyl lower alkoxycarbonyl group, a tri-lower alkylsilyl group and a trityl group, and X is a group represented by the formula: —S—CH$_2$—, —O—CH$_2$— or —CH$_2$CH$_2$—.

7. The compound according to claim 4, wherein:

$R^1$ is a 1-hydroxyethyl group which may be protected by a tri-lower alkylsiliyl group, X is an ethylidene group, $R^2$ is a lower alkyl group, a lower alkenyl group a nitrobenzyl group or a group represented by the formula: —Q—OCOR, wherein Q is a lower alkylene group and R is a lower alkyl group.

8. The compound according to claim 4, wherein the phenyl lower alkyl group is a benzyl group and the phenyl lower alkoxycarbonyl group is a benzyloxycarbonyl group.

9. The compound according to claim 4, wherein X is a group of the formula:

10. The compound according to claim 5, wherein X is a group of the formula:

11. The compound according to claim 7, wherein X is a group of the formula:

* * * * *